(12) United States Patent
Levy

(10) Patent No.: US 11,191,422 B2
(45) Date of Patent: Dec. 7, 2021

(54) MEDICAL SURGERY IMAGING DEVICE USING WIRELESS COMMUNICATION

(71) Applicant: 270 SURGICAL LTD., Netanya (IL)

(72) Inventor: Avraham Levy, Kfar Shmaryahu (IL)

(73) Assignee: 270 SURGICAL LTD., Netanya (IL)

( * ) Notice: Subject to any disclaimer, the term of this patent is extended or adjusted under 35 U.S.C. 154(b) by 288 days.

(21) Appl. No.: 16/332,287

(22) PCT Filed: Aug. 21, 2017

(86) PCT No.: PCT/IL2017/050931
§ 371 (c)(1),
(2) Date: Mar. 11, 2019

(87) PCT Pub. No.: WO2018/060986
PCT Pub. Date: Apr. 5, 2018

(65) Prior Publication Data
US 2019/0200845 A1    Jul. 4, 2019

Related U.S. Application Data

(60) Provisional application No. 62/401,175, filed on Sep. 29, 2016.

(51) Int. Cl.
*A61B 1/00* (2006.01)
*A61B 1/04* (2006.01)
(Continued)

(52) U.S. Cl.
CPC .......... *A61B 1/00016* (2013.01); *A61B 1/00* (2013.01); *A61B 1/00029* (2013.01);
(Continued)

(58) Field of Classification Search
CPC ............ A61B 1/00016; A61B 1/00034; A61B 1/00045; A61B 1/0005; A61B 1/00103;
(Continued)

(56) References Cited

U.S. PATENT DOCUMENTS 8,545,396 B2   10/2013  Cover et al.
9,603,512 B2    3/2017  Hoeg et al.
(Continued)

FOREIGN PATENT DOCUMENTS

WO    2012/078872 A2   6/2012
WO       2016013636    1/2016
WO    2018/100571 A1   6/2018

OTHER PUBLICATIONS

International Search Report PCT/IL2017/050931 Completed Nov. 29, 2017; dated Nov. 30, 2017 5 pages.
(Continued)

*Primary Examiner* — John P Leubecker
(74) *Attorney, Agent, or Firm* — The Roy Gross Law Firm, LLC; Roy Gross

(57) ABSTRACT

A medical imaging device configured to be inserted to a patient's body, comprising an elongated tube, comprising two or more cameras for capturing visual content in the vicinity of the device in different directions of view, a light source for illuminating a field of view of the two or more cameras, a wireless module configured to transmit data captured by the two or more cameras to a remote devices, and a power source for supplying power to the camera, the light source and the wireless module.

11 Claims, 9 Drawing Sheets

(51) Int. Cl.
 *A61B 90/00* (2016.01)
 *A61B 17/00* (2006.01)
 *A61B 90/30* (2016.01)
(52) U.S. Cl.
 CPC ...... *A61B 1/00034* (2013.01); *A61B 1/00181* (2013.01); *A61B 1/042* (2013.01); *A61B 90/361* (2016.02); *A61B 90/37* (2016.02); *A61B 2017/00221* (2013.01); *A61B 2017/00734* (2013.01); *A61B 2090/306* (2016.02); *A61B 2090/309* (2016.02); *A61B 2090/371* (2016.02); *A61B 2090/372* (2016.02)
(58) Field of Classification Search
 CPC ............ A61B 1/00193; A61B 1/00108; A61B 1/00181; A61B 1/0684; A61B 2090/371; A61B 2017/00221
 See application file for complete search history.

(56) References Cited

U.S. PATENT DOCUMENTS

| | | | |
|---|---|---|---|
| 2005/0025368 A1* | 2/2005 | Glukhovsky | A61B 1/04 382/236 |
| 2005/0043583 A1 | 2/2005 | Killmann et al. | |
| 2007/0135684 A1* | 6/2007 | Suzushima | A61B 1/00006 600/160 |
| 2007/0167678 A1* | 7/2007 | Moskowitz | A61B 1/00052 600/104 |
| 2008/0139881 A1* | 6/2008 | Cover | A61B 1/041 600/103 |
| 2010/0081875 A1 | 4/2010 | Fowler et al. | |
| 2010/0198009 A1* | 8/2010 | Farr | A61B 90/53 600/109 |
| 2010/0245549 A1 | 9/2010 | Allen et al. | |
| 2012/0257051 A1* | 10/2012 | Cheng | H04N 7/18 348/143 |
| 2013/0092173 A1* | 4/2013 | Alexander | A61B 1/04 128/207.18 |
| 2013/0253368 A1* | 9/2013 | Are | A61B 1/3132 600/560 |
| 2013/0324794 A1 | 12/2013 | Cover et al. | |
| 2016/0000300 A1 | 1/2016 | Williams | |
| 2016/0150944 A1* | 6/2016 | Tearney | A61B 1/0676 600/109 |
| 2017/0289528 A1* | 10/2017 | Shioda | A61B 1/00193 |
| 2018/0192860 A1* | 7/2018 | Kimura | A61B 1/00045 |
| 2019/0261844 A1* | 8/2019 | Walker | A61B 1/0005 |

OTHER PUBLICATIONS

Written Opinion of the International Search Report PCT/IL2017/050931 dated Nov. 30, 2017 5 pages.
European Search Report for EP Application No. 17855153.7 dated Jul. 8, 2020, 11 pp.

* cited by examiner

MEDICAL SURGERY IMAGING DEVICE USING WIRELESS COMMUNICATION

RELATED APPLICATIONS

This application is a National Phase of PCT Patent Application No. PCT/IL2017/050931 having International filing date of Aug. 21, 2017, which claims the benefit of priority of U.S. Provisional Application No. 62/401,175 filed on Sep. 29, 2016. The contents of the above applications are all incorporated by reference as if fully set forth herein in their entirety.

FIELD OF THE INVENTION

The present invention generally relates to the field of medical instruments inserted to the body and more specifically to the field of medical instruments which are designed to be inserted to the body in some medical procedures, and requires light sources in order to facilitate the medical procedure.

BACKGROUND OF THE INVENTION

An endoscope is a medical imaging device having a light source or light illuminator for emitting light in one end, used to look inside or inspect a region inside a confined area or a specific body cavity or organ. Some endoscopes are inserted into the body through a natural opening, such as the mouth or rectum and are commonly used to detect ulcers, inflammation, erosions, polyps, strictures, malignancies, varices, and bleeding sites. Other endoscopes are inserted into the body by cutting a tissue.

Some of the current solutions utilizing endoscopes have been described in US patent number: 2015/297062 and CN patent 203606564

The need for chirurgic or invasive procedures is not limited to endoscopes. Other medical instruments inserted into the body such as catheters and robotic arms for performing medical surgeries are connected to fibers and cables in order to supply the needed power and/or light and receive the images and digital video transmissions from the cameras located within the medical instrument. Furthermore, other industrial applications such as borescopes may utilize the endoscope technics for mechanical and technical purposes.

SUMMARY OF THE INVENTION

It is an object of the invention to disclose a medical imaging device configured to be inserted to a patient's body, comprising an elongated tube, comprising two or more cameras for capturing visual content in the vicinity of the device in different directions of view, a light source for illuminating a field of view of the two or more cameras, a wireless module configured to transmit data captured by the two or more cameras to a remote devices, and a power source for supplying power to the camera, the light source and the wireless module.

In some cases, the power source is replaceable or rechargeable. In some cases, the wireless module comprises two or more transmitters, each of the two or more transmitters is configured to transmit visual content captured by a specific camera of the two or more cameras. In some cases, each transmitter of the two or more transmitters is configured to transmit visual content associated with a specific predefined area on a display device.

In some cases, the visual content captured by each of the two or more cameras is configured to be displayed on two or more predefined areas on a display device. In some cases, the device is embedded in a robot-assisted surgery device. In some cases, the wireless module is configured to transmit information to multiple remote destinations.

In some cases, the wireless module transmits information in a different channel for each of the multiple remote destinations. In some cases, the medical device further comprises a processor configured to synchronize the timing of transmission of the visual content display to said multiple remote destinations.

In some cases, the processor is configured to compress the visual content captured by said two or more cameras.

In some cases, the tube is flexible. In some cases, the tube is rigid. In some cases, the device is embedded in an endoscope. In some cases, the device is embedded in a catheter. In some cases, the light source comprises at least one LED. In some cases, the light source comprises an optical fiber. In some cases, the two or more cameras are arranged in a manner that enables conversion of the captured visual content into a three-dimensional image.

It is an object of the invention to disclose a medical imaging system, comprising a video receiving system comprising one or more display devices and a wireless receiver, a medical imaging device configured to be inserted into the patient's body, said medical imaging device comprises two or more cameras configured to capture visual content in different directions and a wireless transmitter configured to transmit the captured visual content to the video receiving system, wherein visual content captured by each camera is displayed on a specific area in the one or more display devices.

In some cases, the video receiving system further comprises a system processor, wherein the captured visual content is transmitted from the wireless transmitter to the system processor for processing the captured visual content, and wherein the system processor transmits the processed visual content to the one or more display devices.

In some cases, the system processor is configured to synchronize the timing of the visual content display in said one or more display devices. In some cases, the system processor is configured to decompress the visual content captured by said two or more cameras. In some cases, the system processor is configured to convert the captured visual content into three-dimensional images.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION OF THE INVENTION

The present invention discloses a medical surgery imaging device, also defined as MSID, designed to be inserted directly into the body for medical reasons. The MSID comprises one or more cameras for capturing images or video of a body tissue located in the vicinity of the MSID. The MSID also comprises a wireless transmitter configured to transmit the captured visual content to a remote device, such as a computer or a server, where the visual content may be displayed, analyzed, manipulated or otherwise processed. The MSID also comprises an internal power source located inside a housing. The power source may be a battery configured to provide power to various components of the MSID, such as illumination devices for example LEDs. The MSID may use an internal light source in case the illumination is implemented by transfer of light via a cable inside the MSID. Using an internal power source, a wireless transmitter and sometimes a light source enables the MSID of the present invention to be completely portable, without the requirement of connection to cables for either power, communication or light, as required in prior art medical imaging devices.

The MSID may be designed to be implemented in medical instruments. In some cases, such medical reasons may be examining a body tissue, performing an endoscopy, biopsy, surgery, inject solutions, Laparoscopy, arthroscopy, and the like. In some other cases such medical reasons may be applications such as cardiology diagnostic tests, cardiovascular, neurological, gastrointestinal, neurovascular, ophthalmology procedures, and the like. In possible embodiments of the present invention, the medical instruments may be instruments used to examine the interior of a hollow organ or cavity of the body such as endoscope, anoscope rectoscope, laparoscope, a catheter and the like. In some other embodiments of the present invention the MSID can be integrated into a robotic surgery used in a robot-assisted surgery. Possible embodiments of the present invention may also be implemented in a number of industrial applications such as inspections, or an illumination of a remote object, which are referred to herein as borescopes.

Figure 1:
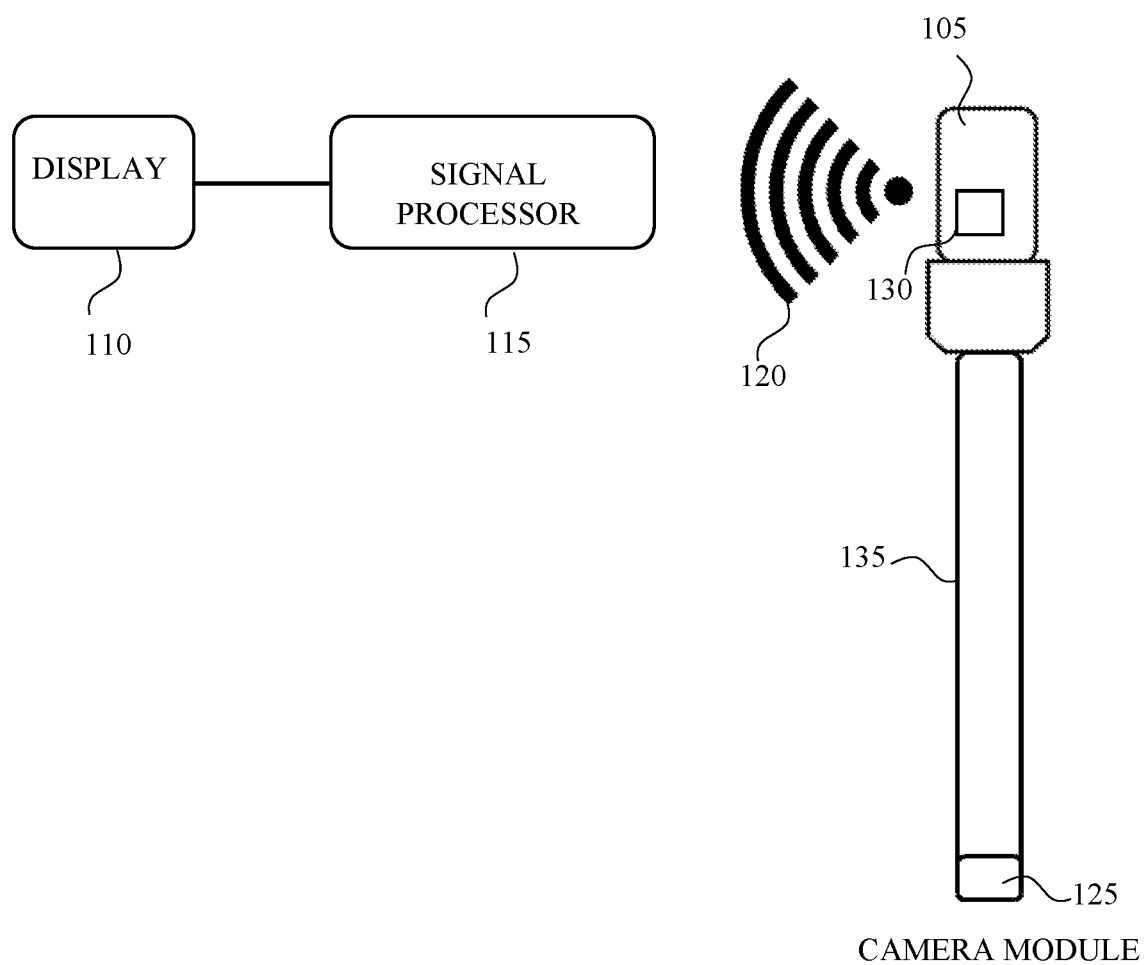
FIG. 1 discloses an MSID connected to a signal processor and a display, according to exemplary embodiments of the present invention.

FIG. 1 discloses an MSID connected via wireless connection to a signal processor and a display, according to exemplary embodiments of the present invention FIG. 1 shows a MSID 105 and MSID tube 135 which comprises a camera module 125 and a wireless module 130. In some cases, the MSID tube 135 may be a rigid or flexible tube of a medical instrument such as, endoscope pipe, a catheter pipe, an integrated part to a surgical robot, or in some cases, an industrial tool such as a borescope. In some embodiments of the present invention, the MSID tube 135 may comprise an additional channel to allow entry of medical instruments. The MSID tube 135 may be utilized in multiple medical procedures which require inserting the medical imaging device directly into a body or a tissue. Thus, the MSID tube 135 is designed to carry a camera such as camera module 125 which can be utilized in said medical procedures. The camera 125 can be any camera utilized in a catheter, endoscope and borescope. In some cases, the camera type may be x-ray camera, video camera, digital image camera, borescope camera, and the like. In some cases, MSID tube 135 may comprise more than one camera module which may be used to provide different views or angles of the tissue.

The wireless module 130 is configured to transmit information from the MSID 105, in a wireless manner, for example to another computer or to a display device. The wireless module 130 may be a wireless transmitter or a wireless transceiver, in case the wireless module 130 is also required to receive signals wirelessly. The wireless module 130 may be connected to a signal processor 115 via wireless channel 120 in order to transmit the visual content captured by camera module 125. Such connection utilized by the wireless module 130 may be based on a WiFi (e.g., 802.11 a/b/g/n) technology, WiMAX, Bluetooth technology, cellular protocols, Infrared technology, and the like.

FIG. 1 also shows a display 110 which can receive the information transmitted by the wireless module 130 and show it. In some cases, the display 110 may comprise a video receiver and a processor which can receive visual content comprising video signals and/or the digital images from the MSID 105, process it to a digital video file or an image file, and display it on the display 110. In some cases, the display 110 may be a video screen, a projector, a computer screen, a mobile computerized device screen, and the like. In some other cases, the display 110 may be connected to a medical machine, such as a surgical robot, receiving the captured images from the MSID, for example when both the MSID and the medical machine are located inside the body.

In cases when the MSID tube 135 comprises more than one camera module, the wireless module 130 may transmit the visual content captured by the camera modules via a dedicated wireless channel assigned to each camera. In some embodiments of the present invention, the signal processor 115 may receive the visual content captured by multiple camera modules from wireless module 130 and then transmit it to multiple displays simultaneously. For example, in case MSID tube 135 comprises 3 camera modules, such as camera module 125, the 3 camera modules can capture visual content from the viewing filed of the MSID 105 and transmit the captured visual content via wireless module 130 to the signal processor 115. The signal processor 115 may transmit the visual content captured by the 3 camera modules to 3 different displays.

In another embodiment, the signal processor 115 may receive the visual content stream captured by multiple camera modules from wireless module 130 and then transmit it to one or more displays simultaneously. For example, in case one display is used, the visual content captured by multiple camera modules from wireless module 130 is then transmitted to a display. While displaying more than one visual content on one or more displays, an indicator may be used to indicate a user about the origin camera of each visual content stream.

In some cases, the 3 camera modules may capture alternative views of the viewing field. Such different alternative views may be different part of the body in the alternative views, different angles of a tissues, same angle of a tissue with different light filters, and the like. In some cases, in which the MSID 105 is integrated into a surgical robot, the signal processor 115 may be able to transmit the visual content also to a robot-surgery console.

Figure 2:
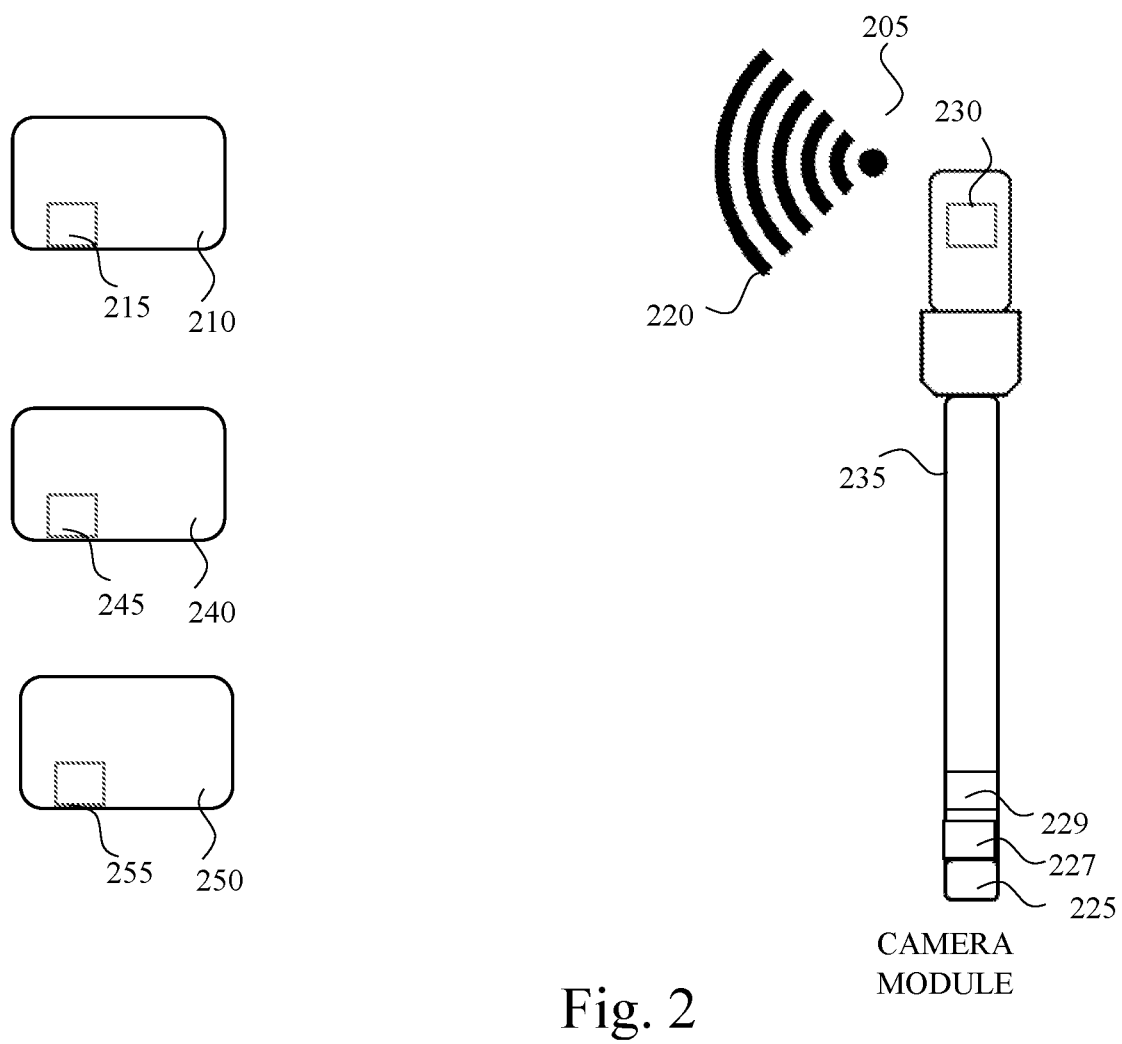
FIG. 2 shows an MSID connected directly to a display, according to exemplary embodiments of the present invention.

FIG. 2 shows an MSID communicating directly to a display, according to exemplary embodiments of the present invention. FIG. 2 shows a MSID 205 comprising an MSID tube 235, a camera module 225 and a wireless module 230. MSID tube 235 is designed to carry a camera such as camera module 225 which can be used in the medical procedures as disclosed above. In some cases, MSID tube 235 may comprise two or more camera modules. The wireless module 230 of the exemplary embodiment communicates directly with a display 210, for example without an intermediate entity such as the signal processor of FIG. 1. In such case, the signal processor 215 may be integrated into the display 210. Thus, the visual content received from the camera module 225 or from multiple camera modules may be transmitted directly to the integrated signal processor 215 via wireless channel 220.

In some cases, in which MSID tube 235 may comprise two or more camera modules. Thus, the wireless module 230 can be configured in order to transmit the visual content captured by the camera modules via dedicated wireless channels for different integrated signal processors. For example, in case MSID tube 235 comprises 3 camera modules, the visual content captured by the 3 camera modules 225, 227, 229 may be transmitted via wireless module 230 to three different integrated signal processors. Then, the integrated signal processors may display the visual content in three different displays, for example displays 210, 240 and 250. The display 240 comprises integrated signal processor 245 and the display 250 comprises integrated signal processor 255. In some embodiments of the present invention the wireless module 230 may be connected with a router or a switch in order to carry out the transmissions of the visual content captured by the cameras. For example, in case wireless module 230 transmits the visual content captured by the cameras to a router, the router may connect with display units such as display 210 and transmit the visual content captured by the camera modules. The switch may be used to send the captured image or video to the appropriate display. For example, images captured by the first camera are sent to the display 210, images captured by the second camera are sent to the display 240, images captured by the third camera are sent to the display 250. In some cases, which the wireless module 230 is connected to a router or a switch, the router or the switch may be connected to a communication network, such as LAN, VLAN, WAN, MAN and the like. In some other cases, in which the MSID tube 235 may be integrated into a robot surgery, the signal processor 215 may be able to transmit the information to the robot-surgery console. In yet another embodiment, the integrated signal processors may display the visual content in one or more displays (not shown). While displaying more than one visual content on one or more displays an indicator may be used to indicate a user about the origin camera of each visual content stream.

In some cases, the wireless module 230 is composed of 2 or more independent modules such that each of them is configured to transmit a single video signal to a different destination. The wireless module may be configured to transmit information to multiple remote destinations. Such remote destinations may be wireless receivers in the video receiving system. The receivers may be located in the same computer, or connected to multiple display devices. For example, each receiver is associated with a different display device, or with a specific area of a display device. In some cases, the wireless module comprises multiple transmitters configured to transmit information in a different channel for each of the multiple remote destinations.

In some cases, the 2 or more independent modules may transmit visual content associated with a shared camera to reduce bandwidth consumption. For example, the MSID comprises two cameras and two wireless transmission modules. The first wireless transmission module transmits content from the center of images or a predefined region of interest of both cameras while the second wireless transmission module transmits the rest of the image. In such case, the MSID comprises a processor for determining the content to be transmitted from each of the two wireless transmission modules.

In some cases, the processor of the MSID identifies redundant content acquired from the two or more cameras. Such content may be the image frame when using stabilization modules, overlapping content that appears in two or more cameras, content outside a predefined region of interest, dark pixels and the like. The processor may remove the redundant content from the content transmitted from the wireless transmission module. The processor may adjust the communication properties in accordance with the removal of content, for example improving image quality if 20 percent of the content is removed.

Figure 3:
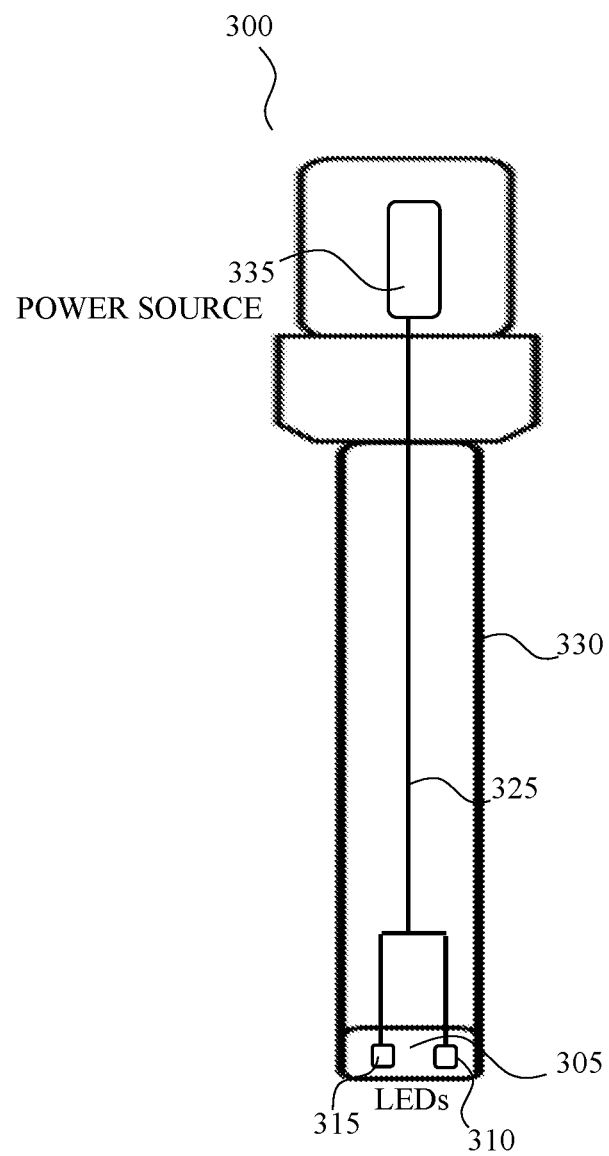
FIG. 3 shows an MSID with an independent power source and independent light source, according to exemplary embodiments of the present invention.

FIG. 3 shows an MSID with an independent power source and independent light source, according to exemplary embodiments of the present invention. FIG. 3 shows an MSID 300 comprises an independent power source 335 located at one side of the MSID tube 330. Such a power source may be an electric battery or a plurality of electric batteries utilized as a power supplier for some internal components of the MSID 300. In some cases, the power source may contain replaceable electric batteries. In some other cases, the electric batteries may be chargeable electric batteries. FIG. 3 also shows a camera module 305 similar to camera module disclosed above in FIG. 1 and may utilize power source 335 as a power supplier. In some cases, MSID tube 300 may comprise multiple camera modules which may utilize the power source 335 as a power supplier via a power cable 325. MSID tube 330 also comprises LED 315 and 310 that may function as a light source for the MSID 300. LED 315 and LED 310 may illuminate the viewing field of the camera module 305, or at least part of said viewing filed. In some cases, LED 310 may be replaceable via MSID tube 330. Thus, MSID tube may comprise a removable top, or a cover that can be opened in order to replace the LED 310 and/or the LED 315.

The LED 310 may be of various illumination types and wavelengths such as UV light used for different medical applications, as detailed below.

Figure 4:
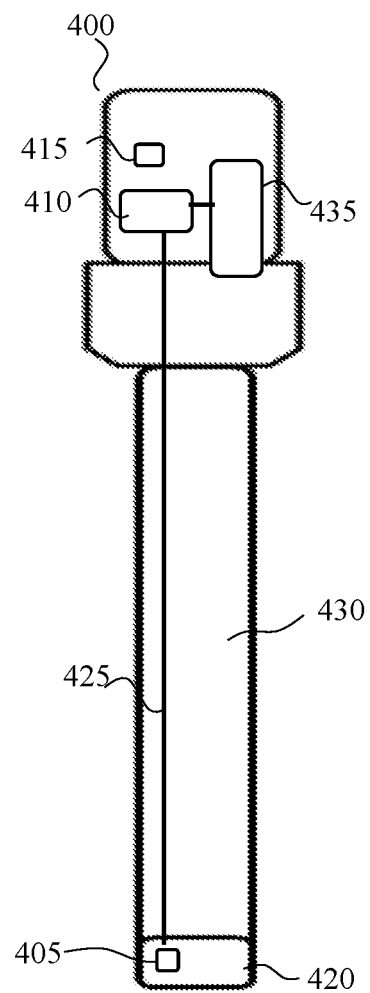
FIG. 4 shows an MSID with an independent light source which illuminating viewing field through an optical fiber, according to exemplary embodiments of the present invention.

FIG. 4 shows an MSID with an independent light source which illuminates a viewing field through an optical fiber, according to exemplary embodiments of the present invention. FIG. 4 shows an MSID 400 comprising MSID tube 430, an independent power source 435, a wireless module 415, and a camera module 420. MSID tube 430 carries a light source 410, the light source is connected to the independent power source 435. In some embodiments of the present invention, a light source 410 may be utilized to illuminate the viewing filed using an optical fiber 425. Thus, MSID 400 may also comprise an optical fiber 425 which may guide the light to the light guide which disperses the light towards the viewing filed of MSID 400. In some cases, the optical fiber 425 may comprise or be connected to a light guide 405 in order to direct the light to a specific location. Light guide 405 may can be made of a flexible tube that can bend, or a rigid tube which can used to guide the light to a specific point or area in the viewing field of MSID 400. In some cases, the light guide 405 may be a replaceable light guide. In some other cases, light filters may be mounted on the light guide 405, such as color filters, wavelength filters, beam splitters and other filters which may be used for certain medical procedures performed using the MSID 400. In some cases, light source 410 may utilize the independent power source 435. For example, a light source 410 may be connected to at least one power source and other components such as camera module 420, wireless module 415, may be connected to a different power source located within the MSID tube 430.

In some cases, the signals transmitted from the MSID are compressed by an image compressing module configured to receive the images from the camera module, or a plurality of camera modules, compress the image and forward the compressed images to the wireless transmitter. The image compression unit may communicate with a signal processor positioned in the MSID that processes the visual content from the camera modules and sends the processed images, before compression, to the image compression unit. In case the images are compressed, the receiving side, the remote devices that receive the images, may comprise a decompression unit for decompressing the images. The need to compress the images results from the need to wirelessly transmit images of high quality, for example HD images, to a remote location, in real time.

In some cases, the information transmitted from the MSID is synchronized, when sending information from two or more camera modules.

Figure 5:
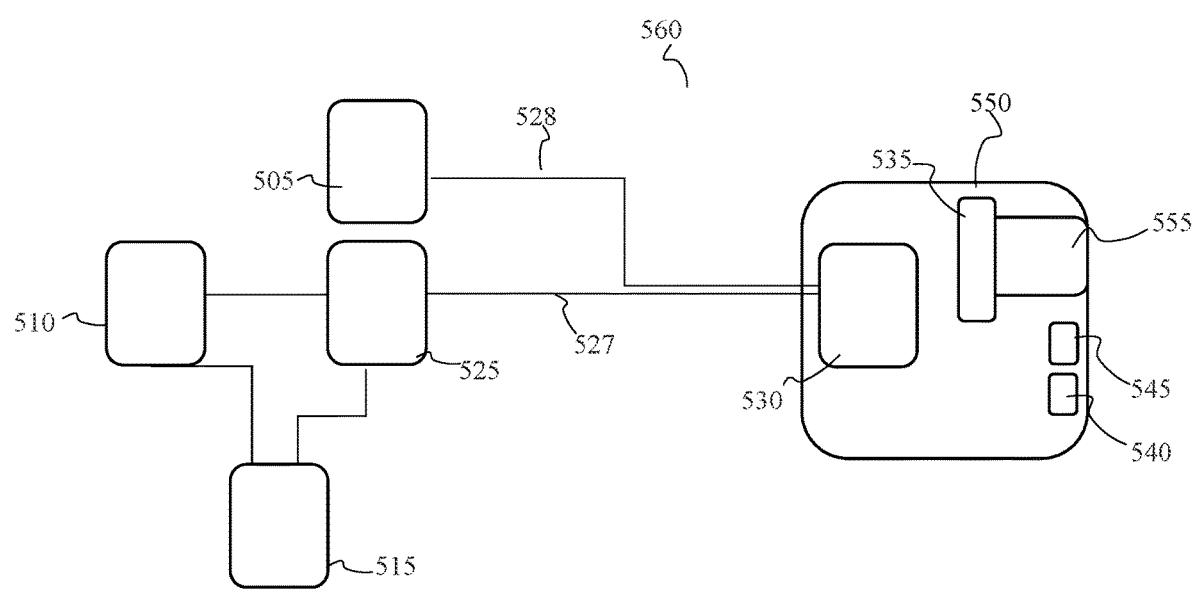
FIG. 5 shows the internal configuration of an MSID, according to exemplary embodiments of the present invention.

FIG. 5 shows the internal structure of an MSID according to exemplary embodiments of the present invention. FIG. 5 shows an MSID 560 which comprises a camera module 550 designed to capture the visual content of the viewing field of MSID 560. For example, in case the MSID 560 is inserted to body or a cavity in the body, the light reflected from the objects existing within the viewing field of the 560, may be captured by camera module 550. Camera module 550 comprises an optical assembly 555 configured to capture the light inserted to the MSID 560 as disclosed above. Optical assembly 555 may have one or in some cases, an array of lenses configured to guide the light from viewing field to the camera module 550. Camera module 550 also comprises an image sensor 535 designed to receive the light inserted to the MSID 560 by the optical assembly 555 and capture it. Camera module 550 also comprises LED 540 and LED 545 configured to illuminate the viewing field of the MSIR 560. For example, LED 540 and LED 545 can illuminate the desired viewing field of the MSID 560, or a part of the desired viewing filed field of the MSID 560. Then, the light reflected from the objects existing within the viewing field may be guided by the optical assembly 555 to the image sensor 535 and captured as an image. Such an image may be an assembly of digital or analog data representing the captured image which can be processed by a computerized device. Camera module 550 also comprises a plate circuit board 530 which electrically connects the components within the camera module 550. Such electrically connects may be the LED's 540 and 545, the image sensor 535, image noise filters and the like. In some cases, the plate circuit board 530 can connect components such as LED's 545 and 540 and image sensor 535 to a power supplier. The plate circuit board 530 may also provide the electrical connections required to electrically transmit the images captured by the image sensor 535, to other components of the MSID 560.

MSID 560 also comprise an image processor 525 configured to receive the image captured by the image sensor 535. The image processor 525 may utilize the connection 527 to receive the images captured by image sensor 535 via the plate circuit board 530. The connection 527 may be implemented as an electrical cable, a flexible printed circuit board or any other electrical solution desired by a person skilled in the art. The image processor 525 may also be connected to wireless module 510 which can receive the image from the image processor 525 and transmit it to external network components as disclosed above. MSID 560 also comprises LED power source 505 designed to deliver the needed current to the LEDs 545 and 540, through electrical connection 528. The current delivered by LED power source 505 may be delivered to LEDs 545 and 540 via the plate circuit board 530. The number of illuminating modules, such as LEDs, may vary according to the MSID configuration or medical procedure. MSID 560 also comprises a power source 515 designed to be a power supplier for the electrical components within the MSID 560. In some cases, the power source 515 can comprise at least one electrical battery which may be a replaceable or chargeable. In some cases, the power source 515 may also function as the LED power source 505.

Figure 6:
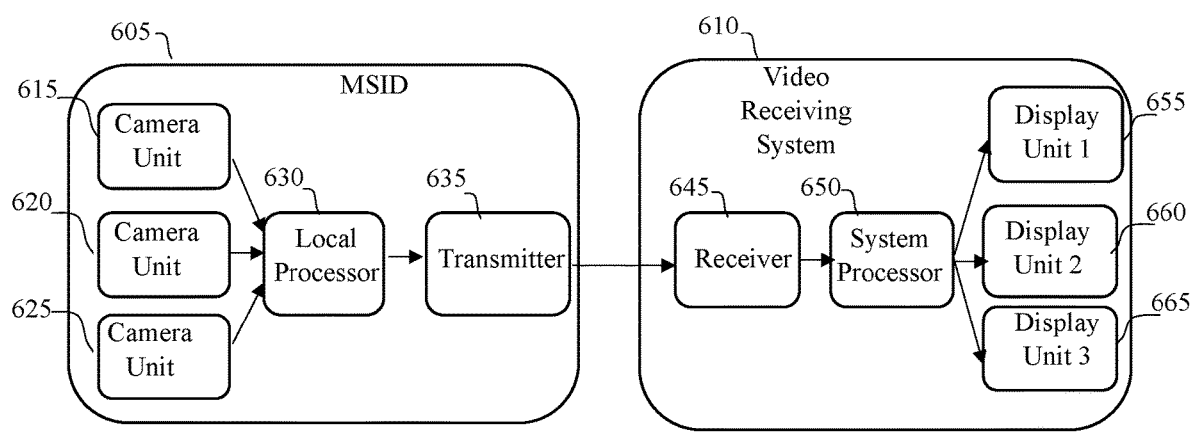
FIG. 6 discloses the architecture of MSID designed to receive the visual content captured by the MSID cameras and to transmit the visual content to a video receiving system, according to exemplary embodiments of the present invention.

FIG. 6 discloses an MSID architecture designed to receive the visual content captured by the MSID cameras and transmit the visual content to a video receiving system, according to exemplary embodiments of the present invention. MSID 605 comprises camera units 615, 620 and 625, configured to capture visual content in the vicinity of MSID 605. In some cases, such visual content received by camera units 615, 620 and 625 can be a video stream. In some other cases, the received visual content may be digital image files or analog data.

MSID 605 also comprises a local processor 630, designed to receive the visual content from camera units 615, 620 and 625 and arrange, process or manipulate the visual content in order to transmit it. For example, the local processor 630 receive visual content from camera units 615, 620 and 625. Then, the local processor 630 may assemble the visual content according to the camera which capture the visual content and transmit it to the transmitter 635. In some cases, the local processor 630 may be able to denote the visual content received from the cameras in order to transmit it to a specific display in the video receiving system 610. The local processor 630 can also assemble the denoted visual content into one unified visual content stream. For example, in an MSID that comprises two cameras, the local processor 630 may be able to denote the visual content received from each camera, assemble the visual content into one unified visual content stream and transmit the visual content stream to be displayed by one or more different displays or screens. In possible embodiments of the present invention, the local processor 630 can be configured to compress the visual content received from each camera. The local processor 630 may also be able to receive the video data from the camera units 615, 620 and 625 and encode it according to standard formats such as, MPEG-2 Part 2, MPEG-4 Part 2, H.264, HEVC, Theora, RealVideo RV40, VP9, AV1, and the like. The local processor 630 can also manage the encoding of single images received from camera units 615, 620 and 625. Such encoding processes may be JPEG, PNG, GIF, and the like. In some other cases, the local processor 630 may also perform some code adjustments such as improve the signal to noise ratio, run quantization process, perform digital signal processing, and the like.

MSID 605 also comprises a transmitter 635 designed to receive the visual content from the local processor 630 and transmit it further to external network components as disclosed above. In some embodiments of the present invention, the transmitter 635 may comprise additional functionalities in order to process the visual content received from the local processor 630. In some cases, the additional functionality may comprise a modulation process in order to allow efficient RF transmission. In some other cases, the transmitter 635 may perform a pre-emphasis process to reduce the effects of noise in the transmitted RF signals. The transmitter 635 is also designed to conduct the wireless transmission to other components in a communication network such as LAN, VLAN, WAN, MAN, WLAN and the like. In some exemplary cases, the transmitter 635 also comprises one or more of the following subsystems: a pre-emphasizer, a sampler, a quantizer, a coder and a modulator.

In some cases the transmitter 635 is customized for a non-standardized and unique communication protocol tailored to optimize system performance. In such case, the receiver 645 is customized to fit to this particular communication protocol.

In some embodiments of the present invention the MSID 605 can comprise one (1), two (2) or three (3) cameras. In other possible embodiments of the present invention the MSID 605 can comprise more than 2 cameras. Thus, the local processor 630 may comprise different configurations in different embodiments of the present invention. In some cases, the local processor 630 may be supported by additional processor and/or a memory units in order to process visual content captured by the cameras.

FIG. 6 also comprises a video receiving system 610 designed to receive the visual content sent by wireless transmitter 635 and display it. The video receiving system 610 comprises a receiver 645 designed to receive visual content transmitted from communication network components, demodulate the received transmission, and extract the video signals out of the carrier wave. The receiver 645 may be a wireless receiver, or a non-wireless receiver, in case another wireless receiver receives the wireless signals from the transmitter 635 and sends non-wireless signals to the receiver 645 of the video receiving system.

The video receiving system 610 also comprises a system processor 650 designed to receive the visual content from the receiver 645 and process it. Such processing may include at least some of the following: decoding the encoded video content and the digital images received from receiver 645, decompressing the visual content received from receiver 645, undo any code modification performed by the receiver 645, and the like. The system processor 650 may also be designed to disassemble the unified stream of visual content received from receiver 645 and identify the denoted visual content received from the cameras within the MSID. In some cases, the system processor 650 may be configured to send the specific visual content received from a specific camera to a specific display. For example, in case of visual content captured by two cameras installed in the MSID received by the receiver 645, the visual content can be delivered from the receiver 645 to the system processor 650. Then, the system processor 650 can disassemble the visual content and transmit the visual content captured by one camera to one display and the visual content captured by the second camera to another display. Yet, the system processor 650 can disassemble the visual content and transmit the visual content captured by one camera to a predefined location on a display and the visual content captured by the second camera to another predefined location on the same display.

The video receiving system 610 is not limited in size and therefore may also be designed for user interfacing features such as freeze, zoom, capture, color balancing and image enhancement.

The video receiving system 610 can also comprise display units 655, 660, 665 configured to receive the video and the imaging content from system processor 650 and present it. Such display units 655, 660, 665 may be a video screen, a television screen, a laptop, a computerized device, a monitor of a robot-assisted surgery device, and the like.

In another embodiment (not shown), video receiving system 610 can also comprise a display unit configured to receive the video and the imaging content from system processor 650 and present it. Such display unit may be a video screen, a television screen, a laptop, a computerized device, a monitor of a robot-assisted surgery device, and the like. In yet another embodiment, video receiving system 610 can also comprise at least one display unit configured to receive the video and the imaging content from system processor 650 and present it. Such at least one display unit may be a video screen, a television screen, a laptop, a computerized device, a monitor of a robot-assisted surgery device, and the like.

In some cases, in which the media unit is a computerized device, the visual content sent to the computerized device may be stored as a computer file. In some cases, the visual content received by the computerized device may not be displayed on a screen.

Figure 7:
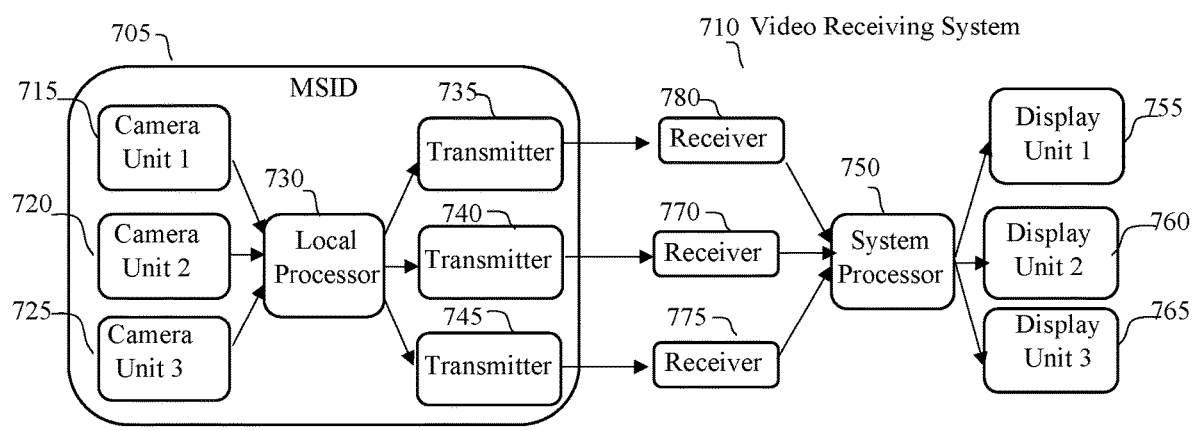
FIG. 7 discloses the architecture of MSID designed to receive the visual content captured by the MSID cameras and to transmit the visual content to multiple receivers in order to display it in multiple devices, according to exemplary embodiments of the present invention; and, FIG. 8 discloses a method for receiving visual content captured by multiple cameras installed within the MSID and displaying it in multiple display units, according to exemplary embodiments of the present invention.

FIG. 7 discloses an MSID architecture designed to receive the visual content captured by the MSID cameras and transmit the visual content to multiple receivers in order to display it in multiple devices, according to exemplary embodiments of the present invention. MSID 705 comprises camera units 715, 720, 725, configured to capture the visual content from the vicinity of the MSID 705. In some cases, such visual content captured by camera units 715, 720, 725 can be video stream or digital image files. MSID 705 also comprises a local processor 730, designed to receive the visual content from camera units 715, 720, 725 and synchronize the visual content in order to transmit it. The visual content captured by camera units 715, 720, 725 can be transferred to the local processor 730. Then, the local processor 730 may timestamp and denote the visual content stream according to the camera which captured the visual content, and transmit it further. In some cases, the local processor 730 may be able to identify the display unit (of the video receiving system 710) associated with each camera in order to transmit the visual content to a specific transmitter. In possible embodiments of the present invention, the local processor 730 can be configured to compress the visual content received from each camera.

MSID 705 also comprises transmitters 735, 740 and 745 designed to receive the visual content from the local processor 730 and transmit it further to a receiver of the video receiving system 710. In some embodiments of the present invention, the visual content captured by the cameras and sent to local processor 730 may be sent to a dedicated receiver connected to a specific video receiving system in similarity to the video receiving system as disclosed above. For example, in an MSID comprising 2 cameras the visual content captured by the cameras can be sent to the local processor 730 and then, the local processor 730 may transmit the visual content to two different transmitters in order to send it out to other components in a video receiving system. In some cases, the local processor 730 may also control the synchronization of the visual content transmitted to the transmitters 735, 740 and 745. Thus, the visual content sent from transmitters 735, 740 and 745 may be seen in a compatible timing on the screens.

In some cases MSID 705 comprises two or more wireless transmitters configured to transmit one stream of image data. The single stream of image data, which may include video data, may later be divided by the local processor into two or more data streams and sent by two or more transmitters to compensate on bandwidth limitation.

FIG. 7 also comprises a video receiving system 710 designed to receive the visual content sent by transmitters 735, 740 and 745 and display it. The video receiving system 710 comprises receivers 780, 770, 775 designed to receive visual content transmitted from transmitters 735, 740 and 745, to demodulate the received transmission, and extract the video signals out of the carrier wave. Thus, the visual content transmitted from the transmitters 735, 740 and 745 can be sent to their corresponding receivers. For example, transmitter 735 can be configured to transmit the visual content to receiver 780, transmitter 745 can be configured to transmit the visual content to receiver 770, and transmitter 740 can be configured to transmit the visual content to receiver 775. The visual content transmission may occur in synchronized fashion, controlled by local processor 730.

In some cases, the system processor 750 is designed to buffer data received from receivers 775, 770, 780. The system processor 750 is designed to output a synchronized image with acceptable latency. This is done by reading the timestamp of each received data and releasing the image data according to the timestamp.

In some exemplary embodiments, the information is transmitted from the MSID in a serial manner. For example, the MSID comprises 3 sensors (S1, S2, S3) and a bandwidth limitation that dictates serial transmission of the data (S1->S2->S3) instead of parallel. For example, the processor may have to wait for the image captured by sensor S3 to arrive and then send all 3 images.

The design disclosed above, with the serial transmission, may be implemented in various manners. For example, sensor S1 is great and very fast and sends the data to the processor 750 before sensor S3. The delay between the times in which the images are received from the sensors may result in allocating more resources to S3, for example by compressing the image received by S1.

The video receiving system 710 also comprises a system processor 750 designed to receive the video content and the digital images from the receivers 780, 770, 775 and process it. In some cases, the video receiving system 710 may comprise multiple system processors 750. In some other cases, a dedicated system processor 750 can be associated with each receiver. The video receiving system 710 can also comprise display units 755, 760, 765 configured to receive the video and the imaging content from system processor 750 and present it. Such display units 755, 760, 765 may be a video screen, a television screen, a laptop, a computerized device, a monitor of a robot-assisted surgery device, and the like. In another embodiment (not shown), the video receiving system 710 can also comprise one or more display units configured to receive the video and the imaging content from system processor 750 and present it. Such one or more display units may be a video screen, a television screen, a laptop, a computerized device, a monitor of a robot-assisted surgery device, and the like.

In some embodiments of the present invention, the communication synchronization may be controlled by the system processor 750. In such cases, the local processor 730 may be configured to denote the visual content received from each camera and transmit the visual content to a dedicated transmitter such as transmitters 735, 740 and 745. The transmitters 735, 740 and 745 may send the visual content to their corresponding receivers such as receivers 780, 770, and 775. The receivers 780, 770, and 775 can send the visual content to multiple display units 755, 760, 765 and the system processor may control the synchronization of the communication to the display units 755, 760, 765. In some cases, the video receiving system 710 may control the display to a number of media units which is larger than three. In some cases, the video receiving system 710 may control the display to a number of media units which is smaller than three.

Figure 8:
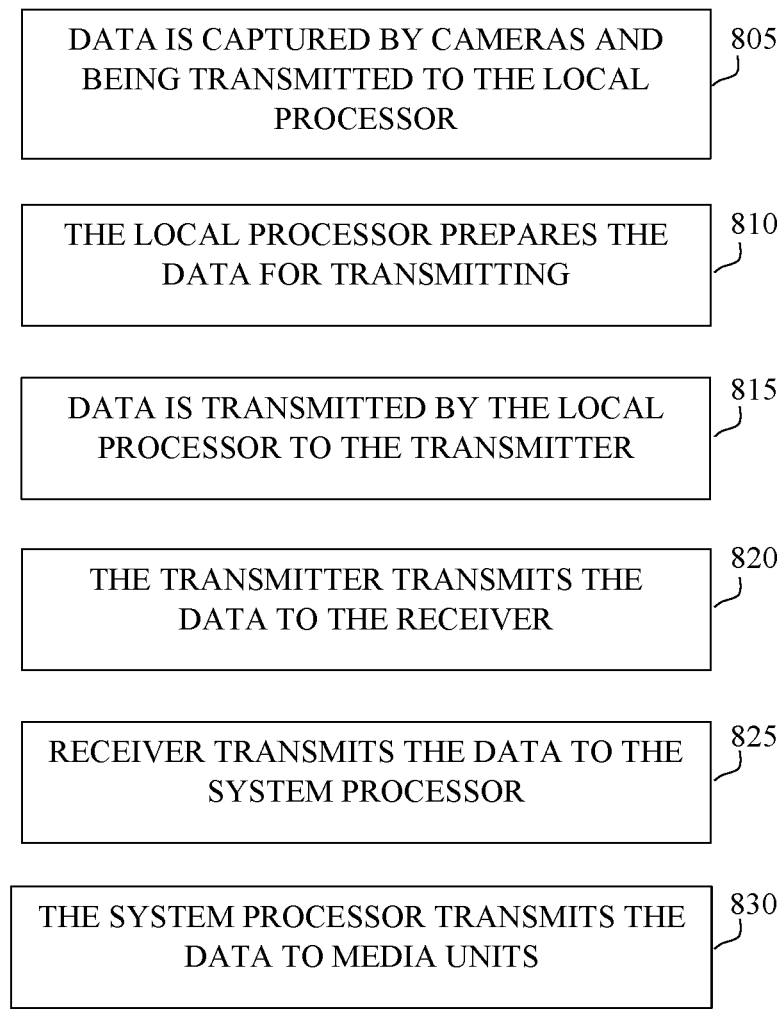

FIG. 8 discloses a method for receiving visual content captured by multiple cameras installed within the MSID and displaying it in multiple display units, according to exemplary embodiments of the present invention. In step 805 the visual content is captured by the cameras installed within an MSID and transmitted to the local processor, as discloses above. Such visual content can be received from multiple camera, or from a single camera. In step 810 the local processor may denote the visual content received from each camera, assemble the visual content to one unified visual content stream and transmit the visual content stream further. The visual content captured by different cameras may be sent to different displays or screens. In some cases, the local processor can be configured in order to compress the visual content received from each camera. The local processor may also be able to receive the video visual content from the cameras and encode it.

In step 815, the visual content is delivered to a transmitter in order to be sent out from the MSID. In some cases, the MSID may comprise more than one transmitter. Thus, the visual content captured by the cameras may be sent separately in order to display different camera contents on different displays. For example, a visual content captured by a camera may be displayed on a dedicated screen and a visual content captured by another camera may be displayed on a different dedicated screen. In yet another embodiment, the visual content captured by the cameras may be sent separately in order to display different camera contents on a display. For example, a visual content captured by a camera may be displayed on a predefined area of a screen and a visual content captured by another camera may be displayed on a different predefined area of the same screen.

In some cases the data coming from one camera may be transmitted by more than one transmitter and reassembled at the receiver side.

Step 820 discloses the visual content captured by the cameras being delivered to a video display system. Thus, the visual content transferred from the transmitter, or from the plurality of transmitters, is received by the receiver. The receiver is capable to demodulate the received visual content and extract the video signals out of the carrier wave. The receiver may send the visual content to the system processor designed to receive the video content and the digital images from the receiver and process it. Such processing may include decoding the encoded video content and the digital images received from the receiver, decompressing the visual content received from receiver, undo any code modification performed by the receiver, and the like. In step 825, the receiver or the plurality of receivers may transmit the visual content to the system processor of the receiving system which may disassemble the unified visual content stream received from the receivers and identify the denoted visual content received from each camera in the MSID. In step 830, the system processor may transmit the visual content to one or more display units. In some cases, the visual content captured by the cameras may be received by multiple receivers. Thus, the system processor may be able to identify the camera and transmit the visual content to a dedicated display. In another embodiment, the visual content captured by the cameras may be received by multiple receivers. Thus, the system processor may be able to identify the camera and transmit the visual content to a predefined area of a display.

The method disclosed above may also comprise a step of synchronizing the visual content captured from a plurality of camera units and configured to be displayed on one or more display devices. Synchronization may be performed by the MSID or by the receiving system.

Figure 9:
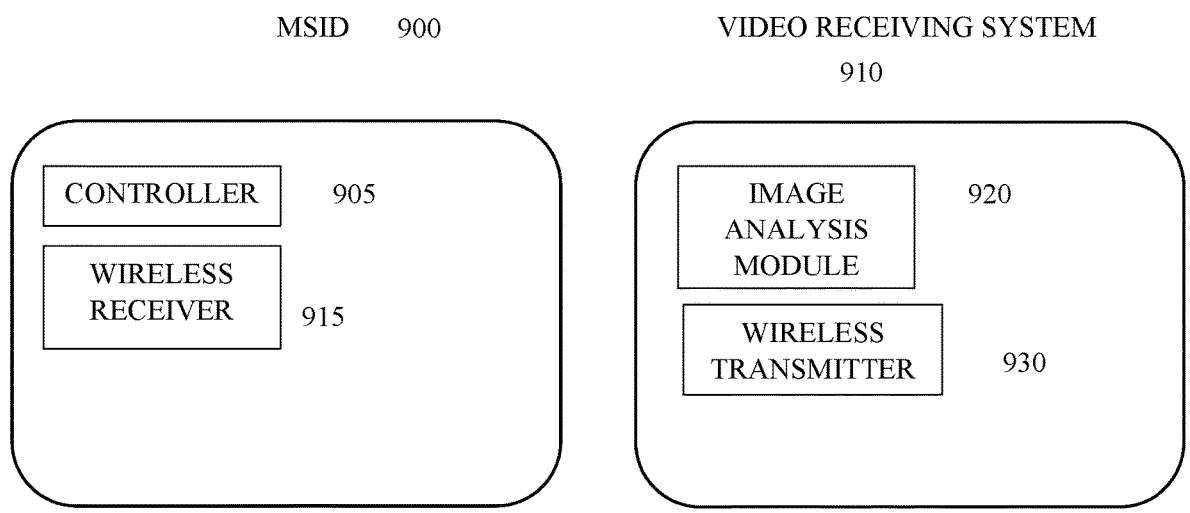
FIG. 9 discloses components of the MSID and the video receiving system designed to improve synchronization and image quality, according to exemplary embodiments of the present invention.

FIG. 9 discloses components of the MSID and the video receiving system designed to improve synchronization and image quality, according to exemplary embodiments of the present invention. The MSID 900 comprises a wireless transmitter as disclosed above, configured to wirelessly transmit visual content to the video receiving system 910, which processes the visual content and displays it. The video receiving system 910 comprises an image analysis module 920 that receives the visual content from the MSID 900 and analyses the content. Such analysis may comprise detecting a light level of the vicinity of the MSID 900 as extracted from the visual content. Such analysis may also comprise image quality, distance between the MSID 900 and a predefined object or tissue in the patient's body, and other properties. The video receiving system 910 outputs an indication on the content that may be sent to the MSID 900 via a wireless transmitter 930 of the video receiving system 910, in a wireless manner. The indication may comprise a command to a component located in the MSID 900, for example a camera, an illumination module, a clock, synchronization unit and the like. The MSID 900 comprises a wireless receiver 915 for receiving the commands and indications from the video receiving system 910 and sending the indications to a controller 925 which sends commands to the electronic components in the MSID.

The invention claimed is:

1. A medical imaging device configured to be inserted to a patient's body, comprising:
    an elongated tube, said tube comprising:
        two or more camera modules placed at one end of the elongated tube and configured to capture visual content in the vicinity of the device in different directions of view, such that the camera modules capture the visual content from different alternative views of a viewing field;
        a light source for illuminating a field of view of the two or more camera modules;
        a wireless module located in the elongated tube configured to transmit data captured by the two or more camera modules to a remote device, and
        a power source for supplying power to the two or more camera modules, the light source and the wireless module;
    wherein the wireless module comprises an image processor configured to receive visual content from each of the two or more camera modules;
    identify a redundant content that appears in the visual content captured by each of the two or more camera modules;
    remove the redundant content from a content to be transmitted;
    assemble the content to be transmitted into one unified visual content stream transmitted from the wireless module to the external device.

2. The medical device of claim 1, wherein the power source is replaceable or rechargeable.

3. The medical device of claim 1, wherein the wireless module comprises two or more transmitters, each of the two or more transmitters is configured to transmit the visual content captured by a specific camera of the two or more camera modules.

4. The medical device of claim 3, wherein each transmitter of the two or more transmitters is configured to transmit visual content associated with a specific predefined area on a display device.

5. The medical device of claim 1, wherein the visual content captured by each of the two or more camera modules is configured to be displayed on two or more predefined areas on a display device.

6. The medical device of claim 1, wherein the device is embedded in a surgical robot or in an endoscope or in a catheter.

7. The medical device of claim 1, further comprises a processor configured to synchronize timing of transmission of the visual content to multiple remote destinations, and wherein the wireless module is configured to transmit information to multiple remote destinations.

8. The medical device of claim 7, wherein the wireless module transmits information in a different channel for each of the multiple remote destinations.

9. The medical device of claim 7, wherein the processor is further configured to compress the visual content captured by said two or more camera modules.

10. The medical device of claim 1, wherein the light source comprises at least one LED.

11. The medical device of claim 1, wherein the two or more camera modules are arranged in a manner that enables conversion of the captured visual content into a three-dimensional image.

* * * * *